(12) United States Patent
Malofsky et al.

(10) Patent No.: US 9,487,468 B2
(45) Date of Patent: Nov. 8, 2016

(54) METHYLIDENE MALONATE PROCESS

(71) Applicant: OptMed Inc., Greenwich, CT (US)

(72) Inventors: Bernard M Malofsky, Bloomfield, CT (US); Chris Mariotti, Unionville, CT (US)

(73) Assignee: OptMed, Inc., New York, NY (US)

( * ) Notice: Subject to any disclaimer, the term of this patent is extended or adjusted under 35 U.S.C. 154(b) by 0 days.

(21) Appl. No.: 14/673,815

(22) Filed: Mar. 30, 2015

(65) Prior Publication Data

US 2015/0203437 A1    Jul. 23, 2015

Related U.S. Application Data

(63) Continuation of application No. 12/774,831, filed on May 6, 2010, now Pat. No. 8,993,795.

(60) Provisional application No. 61/215,610, filed on May 7, 2009, provisional application No. 61/215,578, filed on May 7, 2009, provisional application No. 61/291,898, filed on Jan. 3, 2010.

(51) Int. Cl.
  *C07C 67/54*   (2006.01)
  *C07C 67/62*   (2006.01)
  *C07C 67/343*  (2006.01)

(52) U.S. Cl.
  CPC ............ *C07C 67/343* (2013.01); *C07C 67/54* (2013.01); *C07C 67/62* (2013.01)

(58) Field of Classification Search
  None
  See application file for complete search history.

(56) References Cited

U.S. PATENT DOCUMENTS

| | | |
|---|---|---|
| 2,313,501 A | 3/1943 | Bachman |
| 2,330,033 A | 9/1943 | D'Alelio |
| 3,197,318 A | 7/1965 | Halpern |
| 3,221,745 A | 12/1965 | Coover |
| 3,335,119 A * | 8/1967 | D'Alelio ............ C08F 36/20 522/150 |
| 3,523,097 A | 8/1970 | Coover |
| 3,591,676 A | 7/1971 | Hawkins |
| 3,728,373 A | 4/1973 | Imohel et al. |
| 3,758,550 A * | 9/1973 | Eck ............ C07C 69/52 560/203 |
| 4,049,698 A | 9/1977 | Hawkins et al. |
| 4,056,543 A | 11/1977 | Ponticello |
| 4,160,864 A | 7/1979 | Ponticello et al. |
| 4,291,171 A | 9/1981 | Baum et al. |
| 4,931,584 A | 6/1990 | Bru-Magniez et al. |
| 5,142,098 A | 8/1992 | Bru-Magniez et al. |
| 5,328,687 A | 7/1994 | Leung et al. |
| 5,514,371 A | 5/1996 | Leung et al. |
| 5,550,172 A | 8/1996 | Regula et al. |
| 6,106,807 A | 8/2000 | Albayrak et al. |
| 6,211,273 B1 | 4/2001 | Bru-Magniez et al. |
| 6,420,468 B2 | 7/2002 | Bru-Magniez et al. |
| 6,440,461 B1 | 8/2002 | Bru-Magniez et al. |
| 6,512,023 B1 | 1/2003 | Malofsky et al. |
| 6,610,078 B1 | 8/2003 | Bru-Magniez et al. |
| 6,750,298 B1 | 6/2004 | Bru-Magniez et al. |
| 8,106,234 B2 | 1/2012 | Malofsky et al. |
| 8,609,885 B2 | 12/2013 | Malofsky et al. |
| 8,884,051 B2 | 11/2014 | Malofsky et al. |
| 8,975,435 B2 | 3/2015 | Malofsky et al. |
| 8,993,795 B2 | 3/2015 | Malofsky et al. |
| 2001/0034300 A1 | 10/2001 | Yurugi et al. |
| 2004/0076601 A1 | 4/2004 | Bru-Magniez et al. |
| 2013/0281580 A1 | 10/2013 | Malofsky et al. |
| 2014/0248485 A1 | 9/2014 | Malofsky et al. |
| 2015/0183714 A1 | 7/2015 | Malofsky et al. |

FOREIGN PATENT DOCUMENTS

JP    2008174494 A    7/2008

OTHER PUBLICATIONS

Alejandro Bugarin et. al., "Efficient, Direct α-Methylenation of Carbonyls Mediated by Diisopropylammonium Trifluoroacetate", Chemical Communications, vol. 46, No. 10. p. 1715, 2010.
Diethyl Methylenemalonate. Wayne Feely et al. Organic Syntheses, Coll vol. 4, p. 298; vol. 38 p. 22 (1958).
DI-tert-Butyl Methylenemalonate. Paloma Ballesteros et al. Organic Syntheses, Coll. vol. 7, p. 142 (1990); vol. 64, p. 63 (1986).
2-Methylenedodecanoic Acid. C. Freeman Allen et al. Organic Syntheses, Coll. vol. 4, p. 616 (1963); vol. 38, p. 47 (1958).
Sustained delivery of growth factors from methylidene malonate 2.1.2-based polymers. Laurent Desire et al. Biomaterials 27 (2006) 2609-2620.
Biocompatible poly(methylidene malonate)-made materials for pharmaceutical and biomedical applications. Pascal Breton et al European Journal of Pharmaceutics and Biopharmaceutics XXX (2007)XXX-XXX.
Preparation and Characterization of Novel Poly(methylidene Malonate 2.1.2.)-made Nanoparticles Francois Lescure et al Pharmaceutical Research, vol. 11, No. 9, 1994, p. 1270-1277.
Synthesis and micellization of amphiphilic poly(ethylene oxide)-block-poly(methylidene malonate 2.1.2.) diblock copolymers. Virginie Larras et al Macromol, Rapid Commun. 2000,21, 1089-1092.
Structure elucidation of methylidene malonate 2.1.2 cyclic trimers with mass spectrometry, liquid chromatography and nuclear magnetic resonance investigations. A. Salvador et al Journal of Pharmaceutical and Biomedical Analysis 22 (2000) 165-174.
Über die Polymerisation des Methylenemalonsäurediäthylesters Von H. Hopff et. al. Makromolekulare Chemie, Macromolecular Chemistry and Physics, Jan. 1, 1961, pp. 95-106 (XP008158635).

* cited by examiner

*Primary Examiner* — Sudhakar Katakam
*Assistant Examiner* — Jennifer C Sawyer
(74) *Attorney, Agent, or Firm* — Edward K. Welch, II; IP&L Solutions

(57) ABSTRACT

Novel improved processes for the production and isolation of methylidene malonates via direct and indirect adduct processes.

27 Claims, No Drawings

METHYLIDENE MALONATE PROCESS

RELATED APPLICATION

This application is a continuation of U.S. patent application Ser. No. 12/774,831 filed May 6, 2010, which will issue on Mar. 31, 2015 as U.S. Pat. No. 8,993,795, and which claims the benefit of U.S. Provisional Patent Application Ser. Nos. 61/215,610 and 61/215,578, both of which were filed on May 7, 2009 and entitled "Improved Methylidene Malonate Process," and the benefit of U.S. Provisional Patent Application Ser. No. 61/291,898, filed Jan. 3, 2010, entitled "Methylidene Malonate Process," all of which are hereby incorporated herein by reference in their entirety.

FIELD OF THE INVENTION

The present invention relates to improved processes for the production of methylidene malonates as well as the methylidene malonates produced thereby and the use thereof.

STATE OF THE ART

Methylidene malonates are compounds having the general formula (I):

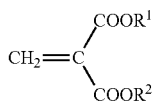

wherein $R^1$ and $R^2$ may be the same or different and represent H or a $C_1$ to $C_{18}$ hydrocarbon group or heterohydrocarbon group having one or more nitrogen, halogen, or oxygen atoms; provided that $R^1$ and $R^2$ are not both H. Such compounds have been known for well over half a century and their value, or more appropriately, potential value and benefit in both organic synthesis and polymer chemistry is well known. Similarly, the use of these compounds as or as a component of adhesives, including skin bonding adhesive; molding materials; and the like is also known. Yet, despite all the promise, these compounds have found limited commercial success owing to the difficulty of their production; the poor, though improving, yet still erratic, yields; and the general instability of these compounds and their production.

Numerous processes have been developed for the production of methylidene malonates having a formula the same as, similar to or falling within the formula of formula (I) above. Two of the earliest methods for the production of methylene di(lower alkyl) malonates, the simplest of the methylidene malonates, were the iodide method in which methylene iodide was reacted with dialkyl malonates and the formaldehyde method in which formaldehyde was reacted with dialkyl malonates in the presence of a base, in solution in alcohol solvents. The former was unsatisfactory due to very low yield and expensive starting materials. The latter, though periodically giving better yields than the iodide process, gave relatively poor yields and, more critically, was widely inconsistent from batch to batch, even under the same conditions.

Despite this inconsistency, early efforts continued to focus on the formaldehyde method. One of the most widely practiced formaldehyde methods consisted of reacting diethyl malonate with formaldehyde in glacial acetic acid in the presence of a metal acetate catalyst to produce the diethyl methylidene malonate. The latter was subsequently recovered by distillation following removal of the catalyst by filtration and separating off the solvent. These efforts continued to frustrate and various modifications and iterations of this basic process were developed all in an effort to improve the consistency and yields associated therewith.

Bachman et. al. (U.S. Pat. No. 2,313,501) taught the reaction of a $C_1$-$C_5$ dialkyl malonate with formaldehyde in the presence of an alkali metal salt of a carboxylic acid, in solution in a substantially anhydrous carboxylic acid solvent, followed by fractional distillation to separate the desired product. Bachman et. al. indicate that their process is advantageously carried out in the presence of inhibitors of the polymerization of monomeric vinyl compounds. Suitable inhibitors are said to include the copper salts such as copper chloride and, especially, copper salts of carboxylic acids such as cupric acetate, iron salts such as ferric acetate, and phenols, such as hydroquinone. These are added to the solution mix before the addition of the malonate.

Although Bachman et. al. reported yields of up to 72%, the results presented are conversion rates, not yields. Looking at the actual yields of the process, Bachman et. al.'s best performance was a yield of 43% with all others being less than 25%. Though Bachman et. al. speak of high purity and the ability to recover pure material, they never present any details or data as to what those purities or recoveries were. In any event, Bachman et. al. reported that the isolated product, upon standing, polymerized in a day to several weeks time depending upon the purity of the isolated material, which polymer was then heated to facilitate the reversion of the polymer to the monomer.

D'Alelio (U.S. Pat. No. 2,330,033), on the other hand, alleged that such processes were erratic and more often produced yields that averaged 10 to 12 percent. D'Alelio espoused an improved process with yields on the order of 30% and higher by reacting a malonic acid ester with formaldehyde in a ratio of one mole of the former to at least one mole of the latter under alkaline conditions and, in most cases, in the presence of a polymerization inhibitor such as copper, copper acetate, hydroquinone, resorcinol, or catechol, to form a methylol derivative. The methylol derivative is then acidified to a pH below 7.0 using a suitable organic or inorganic acid in order to retard further reaction. The acidified mass is then dehydrated to form the corresponding methylidene malonate which is subsequently separated by distillation.

Coover et. al. (U.S. Pat. No. 3,221,745 and U.S. Pat. No. 3,523,097) took another approach to the formation of the methylidene malonates, electing to begin with a preformed dialkyl alkoxymethylenemalonate. In accordance with their process, the olefinic double bond of the latter compound was subjected to hydrogenation in the presence of a hydrogenation catalyst and the hydrogenated compound was then subject to pyrolysis in the presence of a phosphorous pentoxide inhibitor to strip off the alcohol to produce the methylene malonate. The resultant mass was then subjected to vacuum distillation at low temperature to separate an allegedly high purity methylidene malonate, though with a low yield. According to Coover et. al., the use of low temperature distillation is said to prevent the contamination of the monomer with pyrolytic products that commonly result from high temperature distillation. These high purity monomers are said to be especially important for surgical applications.

In discussing the critical need for high purity materials, Coover et. al. draw particular attention to the extreme sensitivity of their monomers to the presence of even small amounts of acidic and basic impurities, the former inhibiting polymerization leading to sluggish and ineffective adhesive activity and the latter accelerating polymerization leading to unstable and useless products. They indicate that the amount of such impurities should not exceed 100 ppm, preferably not more than 10 ppm. Unfortunately, other than discussing its limitations with respect to the acidic and basic impurities, and despite its contention of high purity materials, Coover et. al. never provide any data pertaining to the purity of their materials. Clearly, though, they are not "pure" materials inasmuch as they, like the others before them and since, require redistillation of the "pure" distillate.

Additionally, although suggesting that their high purity materials "have reasonably good" stability when stored in bulk, they recommend the addition of low levels, 0.0001 to 0.01 weight percent, of a polymerization inhibitor to the monomer materials in order to increase storage stability. Suitable polymerization inhibitors are said to include sulfur dioxide, hydroquinone, nitric oxide, organic acids, boron trifluoride, hydrogen fluoride, stannic chloride, ferric chloride, and organic anhydrides. To assist with cure, particularly cure speed, Coover et. al. also suggest the addition of cure accelerators or catalysts to their formulated adhesives, but cautions against adding them too early as they would cause premature polymerization.

Despite the erratic nature of the aforementioned processes, there were continued efforts to find improved processes for the production of methylidene malonates with a focus on more consistent and reliable processes with improved yields and higher purity. These effort focused not only on the simple methylidene malonates of the early art but also on finding new routes that allowed for the formation of a broader array of methylidene malonates, including symmetrical and asymmetrical species as well as those whose ester functionality was more complex, e.g., having a higher carbon number, unsaturation, heteroatoms and the like.

Eventually, such efforts led to multi-step processes in which certain unsaturated molecules served as a platform for the formation of intermediate adducts from which the methylidene malonates were subsequently stripped and recovered. For example, Hawkins et. al. (U.S. Pat. No. 4,049,698) found that certain malonic diesters could be reacted with formaldehyde and a linear, conjugated diene in the presence of a primary, secondary or tertiary amine at about reflux temperature to form an intermediate adduct that could then be readily pyrolyzed at temperatures in excess of 600° C. to split off the desired methylidene malonate. Ponticello (U.S. Pat. No. 4,056,543) and Ponticello et. al. (U.S. Pat. No. 4,160,864) developed processes by which asymmetrical methylene malonates, especially methyl allyl methylene malonate, were prepared from previously formed norbornene adducts, the latter having been prepared by the Diels-Alder reaction of an alkyl acrylate with cyclopentadiene at room temperature or with heating or use of a Lewis catalyst. The so formed monoester norbornene adducts were then reacted with an electrophile material in the presence of an alkyl-substituted lithium amide complex to form the diester adduct and subsequently pyrolyzed at a temperature of 400° C. to 800° C. at a pressure of 1 mm to 760 mm Hg in an inert atmosphere to strip off the desired methylene malonates. These efforts, despite their gains in yield and/or purity, still failed to achieve commercial success.

Citing numerous disadvantages of the foregoing processes, which disadvantages were said to make them difficult, if not impossible, to adapt to industrial scale, Bru-Magniez et. al. (U.S. Pat. No. 4,932,584 and U.S. Pat. No. 5,142,098) developed a process whereby anthracene adducts were prepared by reacting mono- or di-malonic acid ester with formaldehyde in the presence of anthracene, most preferably in a non-aqueous solvent medium in the presence of select catalysts. According to Bru-Magniez et. al., the anthracene adducts were said to be readily produced in high yields with the desired methylidene malonates obtained by stripping them from the anthracene adduct by any of the known methods including heat treatment, thermolysis, pyrolysis or hydrolysis; preferably heat treatment in the presence of maleic anhydride. The resultant crude products were then subjected to multiple distillations, preferably lower temperature distillations under vacuum, to recover the purified methylidene malonate. Despite the claim to high yields, their crude yields were generally in the range of 21-71%, more importantly, nothing is said with respect to the purity of the material obtained.

Based on conversations with the successors to the Bru-Magniez technology, efforts to commercially produce the material have met with great difficulty owing to the high instability of the overall production process and final products. Indeed, they reported a high failure rate: of the limited batches that actually survived through crude distillation, the resultant products had to be stored in a freezer even after stabilizing with upwards of 50,000 ppm $SO_2$ due to their high instability and spontaneous polymerization. Indeed, our own attempts to follow the prior art processes, including the Bru-Magniez process, most often resulted in failure owing to sublimation of the paraformaldehyde, a failure to produce the desired product (as evidenced by a lack of double bonds in the reaction product), and, more frequently, polymerization of the reaction mix and/or the crude yield. Even when a successful run was realized, it has now been found that the purity of the materials was quite low. Though the traditional analytical tests employed, including, the boiling point, fraction temperature, and refractive index suggests good yield and purity, further, more sophisticated analysis has found that these reaction products actually contained a number of analogs of the desired methylidene malonate, in addition to the desired material, as well as various byproducts. For example, in our efforts to produce 1-ethoxycarbonyl-1-ethoxycarbonyl methylene oxycarbonyl ethane (the 2.1.2 monomer), we found that besides the 2.1.2 monomer, the reaction products, even after initial separation and distillation, contained substantial amounts of the di-substituted and unsubstituted analogs (the 2.1.1.2 and 2.2 analogs, respectively) and oligomers and polymers of the foregoing, as well as various byproducts, especially glutarates. Consequently, though yields were presumably higher than achieved by other methods, purity was not as high as hoped and, as found through subsequent effort, repeatability was erratic at best.

While the use of intermediate adducts promoted higher yields and allowed greater versatility, particularly with respect to the broader variety of methylidene malonates capable of being produced, lingering problems persisted, namely batch-to-batch inconsistency and the general instability of the process as well as the so-formed crude and final products, especially in bulk storage, and of formulated products, such as adhesives, made with the same. Additionally, the adduct routes involve considerable added expense, particularly in light of the need for the additional reactants and other materials, added production steps and time, new energy requirements and environmental concerns, and the like. Furthermore, despite their advances, these processes have yet to fully or even adequately address, particularly from a commercial viability standpoint, the underlying and critical problems evidenced by the continuing inconsistency in the production of the methylidene malonates, particularly as reflected by the ongoing instability of the reaction mix particularly during the distillation and recovery of the desired product as well as of the recovered product. It is this erratic nature of the production process and resultant product and the attendant costs associated therewith that compromises and overshadows the commercial value and opportunity for these products.

If the methylidene malonates are ever to realize their commercial potential and promise, particularly in applications other than niche, high value added applications whose pricing can better offset the losses, costs and low yields of current processes, improved processes must be developed, especially processes that provide for more consistent and predictable yields. However, it has also been found that yield alone is not sufficient. Indeed, it has now been found that purity of the monomer, purity that goes far beyond the concerns with acidic and basic impurities as forewarned by Coover et. al., plays an important role in the cure or polymerizable characteristics of these materials and, perhaps most importantly, the properties of the polymerized materials. This is especially true for adhesive type applications for these materials.

Thus, there is a need for processes for the production of methylidene malonates that are not fraught with process failures, widely varying yields, unstable products, and unintended polymerizations and other by-products. Additionally, it would be desired to provide such processes that avoid the need for intermediate adducts and their related additional process steps, materials requirements, wastes and waste streams as well as the concomitant time and energy requirements associated therewith.

There also remains a need in the industry for a viable commercial scale adduct-free process for the production of methylidene malonates that provides good to high yields with, most notably, high purity, and most preferably on a consistent and predictable basis.

Furthermore, there remains a need in the industry for improved processes for the adduct-free production of methylidene malonates wherein the formation of byproducts, such as glutarates, and dimers, oligomers and polymers of the methylidene malonates as well as thermal degradation products of the foregoing and the starting reactants, are lessened, if not avoided, particularly during the separation and fractionation steps for the recovery of the methylidene malonates.

In particular there is a need for a process that consistently achieves crude yields in excess of 20%, preferably in excess of 30%, more preferably in excess of 35%, most preferably of about 40% or more, especially with purities of the desired product and its analogs on the order of 80%, preferably 90% or more. Indeed, it would be phenomenal to attain purified yields on the order of 30% or more, let alone 40% or more, wherein the resultant product contained less than 8%, preferably less than 6%, most preferably less than 4%, of impurities and less than 12%, preferably less than 10%, most preferably less than 8% of the analogs of the desired product, on a consistent basis, and most preferably without the use of an intermediate adduct.

Similarly, and in following therewith, there is a ongoing need for methylidene malonates whose bulk and long term storage stabilization is attained without concern for, or certainly less concern with respect to, the impact of such stabilization on the subsequent polymerization characteristics of the so formed methylidene malonates. In particular, there remains a need and desire for methylidene malonates that do not require further processing, such as degassing or the addition of scavengers, to remove stabilizers and polymerization inhibitors before the methylidene malonates can be formulated into end-use products and/or used in their intended end-use applications.

Finally, there is a need and desire for methylidene malonates that do not require, or require less, catalyst, polymerization activator and/or accelerator and the like, than heretofore required, in order to attain a sufficient degree and/or speed of polymerization, especially in adhesive and like bonding applications.

SUMMARY OF THE INVENTION

According to a first aspect of the present invention, there are provided improved adduct-free processes for the production of methylidene malonates wherein the improvement comprises the addition of a reaction phase stabilizer system comprising one or more anionic polymerization inhibitors, at least one of which must be a liquid phase anionic polymerization inhibitor, most preferably an acid, especially an organic or sulfonic acid, alone or in combination with at least one free radical polymerization inhibitor, to the reaction mix and/or the crude reaction product, wherein, in the latter case, the stabilizer system is added just prior to, concurrent with or following completion of the formation of the methylidene malonate. Preferably, the reaction phase stabilizer system is added to the crude reaction product concurrent with or, more preferably, immediately following removal of the solids components contained therein, e.g., catalyst, and/or washing of the crude reaction product. In any event, the reaction phase stabilizer system should be added to the crude reaction product prior to storing the crude reaction product or the remaining crude liquid reaction product or prior to subjecting the crude product or the remaining crude liquid reaction product to any fractionation process, most notably any fractionation steps that involve heat and/or long periods of standing, even at room temperature. In those instances where both an anionic polymerization inhibitor and a free radical polymerization inhibitor are used, the former may be added to the reaction mix prior to or during the reaction for the production of the methylidene malonates and the latter to the crude reaction product or, more preferably, to the crude liquid reaction product. Most preferably, the reaction phase stabilizer system is added to the crude liquid reaction product remaining after removal of the solids from the crude reaction product and, if employed, solvent washing steps, but before fractionation to isolate and/or purify the methylidene malonate.

According to a second aspect of the present invention, there is provided an improved process for the separation and isolation, i.e., the purification, of methylidene malonates produced in an adduct-free process, wherein the improvement comprises the addition of a separation phase stabilizer system to the materials to be purified as well as the separated or purified methylidene malonate material. The separation phase stabilizer system may be the same as the reaction phase stabilizer system or a different stabilizer system comprising components suitable for use as a reaction phase stabilizer system or it may comprise at least one secondary anionic polymerization inhibitor, alone or in combination with one or more free radical polymerization inhibitors. As with the reaction phase stabilizer system, the separation phase stabilizer system also has at least one liquid phase anionic polymerization inhibitor.

While the separation phase stabilizer may be added to the collected material arising from the separation or fractionation process following its collection, it is preferred that at least a portion of the separation phase stabilizer system be added to the collection flask or vessel prior to initiation of the separation process and the remainder added to the collected material following completion of the collection. The amount of the separation phase stabilizer system to be added to the empty collection flask or vessel will be based on the projected amount of material to be collected: generally the amount will be somewhat less than that needed if the full amount projected to be recovered were to actually be recovered. Once the separation is completed, the amount of separation phase stabilizer is then adjusted upward, as appropriate, based on the actual amount collected. This same process, i.e., the addition of the separation phase stabilizer system, will be used for each successive separation or purification step employed, if any.

In yet a third embodiment of the present invention, there is provided an improved overall process for the production and recovery of methylidene malonates, from malonate reactant or precursor to purified methylidene malonate, which process employs both a reaction phase stabilizer system in the reaction phase of the methylidene malonate production process and a separation phase stabilizer system in the separation, purification, and recovery phase of the methylidene malonate production process.

As noted above, the present invention is especially applicable to those processes for the preparation of methylidene malonates based on various condensation reactions of a malonate reactant or precursor, especially those processes involving a Knoevenagel type condensation reaction. In particular, the present invention is especially applicable to those Knoevenagel type condensation reactions based upon the reaction of a malonate with formaldehyde, paraformaldehyde or the like, in the presence of an acid, particularly glacial acetic acid, and a suitable catalyst and typically in the presence of a suitable solvent.

By implementing the improved processes as set forth herein, one realizes more consistent and/or improved yields. For example, one may attain crude yields in excess of 25%, preferably in excess of 35%, more preferably in excess of 40%, most preferably in excess of 50% or more, on a consistent and repeatable basis. Most importantly, these yields are attained with a concomitant high purity, generally 60% or more, preferably 75% or more, more preferably 80% or more, most preferably 90% or more, with or without the use of the intermediate adducts. More importantly, the further fractionation of these yields by the improved separation process and associated separation phase stabilizer system results in even higher purities with excellent yields. Generally, one is able to realize purified yields in excess of 20%, preferably in excess of 30%, more preferably in excess of 35%, most preferably of about 40% or more, based on the original malonate reactant, on a repeatable and consistent basis. Furthermore, these "purified" fractions or collections of methylidene malonate generally have purities exceeding 80%, preferably 85%, more preferably 90%, most preferably 95%. Thus, even if the yields, especially the purified yields, slip below the aforementioned targets, the loss in yield is more than made up for by the increased purity attained with the improved processes. Hence; yields as low as 15%, even 10%, with high purity of 85% or higher, preferably 90% or higher, most preferably 95% or higher, provides a suitable process and is within the scope of the present invention. Generally speaking, the improved processes of the present invention provide for high purity wherein the purified product contains less than 8%, preferably less than 6%, most preferably less than 4%, of impurities and less than 12%, preferably less than 10%, most preferably less than 8% of the analogs of the desired product, on a consistent basis.

In accordance with another aspect of the present invention there are provided stable, high purity methylidene malonates, in crude and/or purified form, produced by any of the foregoing improved methods.

Finally, in accordance with yet another embodiment of the present invention there are provided methylidene malonate adhesive compositions comprising the methylidene malonates prepared in accordance with the foregoing processes.

DETAILED DESCRIPTION OF THE PREFERRED EMBODIMENTS

According to the present invention there are provided improved processes for the production and/or separation and recovery of methylidene malonates, particularly improved adduct-free processes. Methylidene malonates are compounds having the general structure (I):

wherein $R^1$ and $R^2$ may be the same or different and represent H or a $C_1$ to $C_{18}$ hydrocarbon group or heterohydrocarbon group having one or more nitrogen, halogen, or oxygen atoms; provided that $R^1$ and $R^2$ are not both H. Preferably each $R^1$ and $R^2$ are each independently a $C_1$ to $C_{10}$, most preferably a $C_1$ to $C_6$, linear or branched alkyl group; a $C_3$ to $C_6$ alicyclic group; a $C_2$ to $C_6$ alkenyl group; or a $C_2$ to $C_6$ alkynyl group; any of which may optionally be substituted with an ether, epoxide, halo, ester, cyano, aldehyde, ketone or aryl group. A further preferred subset of methylidene malonates are those wherein one or both of $R^1$ and $R^2$, which may be the same or different, are of the formula (IV):

$$—(CH_2)_n—COOR^8 \qquad (IV)$$

wherein $R^8$ is a $C_1$ to $C_6$, preferably a $C_1$ to $C_6$, lower alkyl and n is an integer of from 1 to 5, preferably 1 or 2: said ester group most preferably having been formed as a result of an ester exchange reaction.

As used herein and in the appended claims, the term "adduct-free" refers to those processes for the production of methylidene malonates that do not involve the formation or use of intermediate diene or polynuclear aromatic adducts. Similarly, as used herein and in the appended claims, the term "crude product" or "crude yield" means that reaction product containing the intended methylidene malonate prior to any separation or isolation steps to remove the non-liquid components, e.g., catalyst and catalyst residue. As context allows, it may also mean that liquid reaction product remaining after separation, whether by filtration, crude distillation or the like, of the liquid materials from the solids in the reaction product mix: although this is oftentimes referred to as the crude liquid product. Also, as used herein the term "initial re-distillation" or "second distillation" refers to the initial distillation of the crude yield, i.e., crude liquid monomer distilled from or otherwise separated from the reaction mix. The term "fractionation" is used herein to mean the act or process of separating, isolating and/or purifying the methylidene malonate from the liquid phase of the crude reaction product, most notably, from the crude liquid reaction product, as well as any subsequent steps or processes to further increase the purity thereof. Further, when referencing the amount of polymerization inhibitors to be used, the amount is presented in parts per million (ppm) based on the weight of the malonic acid or malonate precursor (unless otherwise indicated) in the case of the reaction phase polymerization inhibitors and on the theoretical weight of the recoverable methylidene malonate in the case of the separation phase polymerization inhibitors, unless otherwise indicated. Finally, it is to be noted that the terms "stabilizer" and "polymerization inhibitor" are used interchangeably herein: each having the same intended definition.

Adduct-free processes for the production of methylidene malonates are well known: a number of such processes having been discussed and described in those patent publications set forth in the background section above, all of which are hereby incorporated herein by reference in their entirety. The present invention is especially applicable to those processes for the preparation of methylidene malonates based upon a condensation reaction of a malonate or malonate precursor. For example, it is applicable to those processes wherein a dialkyl alkoxy methylene malonate is hydrogenated and subsequently subjected to distillation or heat in order to remove the alcohol and leave the methylidene malonate. Such processes are disclosed in Coover et. (U.S. Pat. No. 3,221,745 and U.S. Pat. No. 3,523,097) as well as in Freely et. al., Organic Syntheses, Coll. Vol. 4, p. 298 (1963); Vol. 38, p. 22 (1958), which are hereby incorporated herein by reference.

The present invention is especially applicable to those processes for the production of methylidene malonates involving a Knoevenagel type condensation reaction of a malonate or malonate precursor with a formaldehyde source in the presence of an appropriate catalyst, alone or in combination with an acid, especially acetic acid, and, most typically, a suitable solvent. Though, it is to be appreciated that the acid may also serve as a suitable solvent fort the reaction.

The present invention is applicable to malonate esters generally. Suitable malonates include those of the general structure (II):

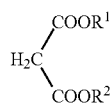

(II)

wherein $R^1$ and $R^2$ are as defined above. Formaldehyde sources include, but are not limited to formaldehyde, paraformaldehyde, formalin, gaseous formaldehyde. The amount of the formaldehyde source is preferably such that the mole ratio of malonate to formaldehyde (or formaldehyde equivalent) is from about 1:0.7 to about 1:2, preferably from about 1:0.8 to about 1:1.4, most preferably from about 1:0.9 to 1:1.2. It is believed that a molar excess of the formaldehyde or formaldehyde source overcomes loss of formaldehyde due to sublimation owing to the long reaction times.

Suitable catalysts include primary, secondary and tertiary amines, especially secondary aliphatic amines; particularly where the platform is a conjugated diene. Exemplary amine catalysts include piperidene, piperazine, N-methylpiperazine, dibutylamine, morpholine, diethylamine, pyridine, triethylamine, tripropylamine, triethylenediamine, N,N-dimethylpiperazine, butylamine, pentylamine, hexylamine, heptylamine, nonylamine, decylamine, and the like. Especially preferred amines include piperidene, piperazine, N-methylpiperazine, dibutylamine, morpholine, and diethylamine. The salts of these amines with organic monocarboxylic acids, such as piperidine acetate, also act as effective catalysts.

Preferably, the catalyst is a metal or metal salt, most preferably a metal salt of a lower monocarboxylic acid. Such catalysts include the Rainey nickel catalysts, zinc chloride, copper(II) acetate, cupric acetate monohydrate, potassium acetate, zinc acetate, zinc chloracetate, magnesium chloracetate, magnesium acetate, and combinations of any two or more thereof, especially copper(II) acetate, potassium acetate and combinations of the two. The catalysts are generally present at from 0.1 to about 35, preferably from about 0.5 to about 20, weight percent based on the weight of the malonate ester. Surprisingly, it has now been found that the amount of catalyst used can be considerably less than previously used or thought necessary, perhaps as low as 10% of that previously used. For example, from about 1 to about 14, preferably from about 3 to about 10, weight percent catalyst based on the weight of the malonate seemed to produce better yields as compared to those with catalyst amounts in the higher end of the aforementioned general range, i.e., above 20 weight percent.

Most preferably, when the catalyst is a metal or metal salt, there is also present an acid, most preferably acetic acid, acetic acid anhydride, or glacial acetic acid. This is especially so for the copper based catalysts. The amount of acid is preferably such that the mole ratio of malonate to the acid is from about 1:0.8 to about 1:2, preferably from about 1:0.9 to about 1:1.5, most preferably from about 1:1 to 1:1.4.

Although non-aqueous solvents are preferred, the reactions may be conducted in either an aqueous or a non-aqueous medium. Advantageously, the non-aqueous medium may be a water miscible solvent, a water immiscible solvent, or a combination of at least one water miscible solvent and at least one water immiscible solvent: the choice being dependent upon the particular system and materials employed. Exemplary non-aqueous solvents include, but are not limited to, acetic acid, acetic anhydride, glacial acetic acid, benzene, bromobenzene, xylene, toluene, dimethylformamide (DMF), dimethylsulfoxide (DMSO), tetrahydrofuran, a ketone such as dimethyl ketone or ethylmethyl ketone, alkanes such as heptane and hexane, acetonitrile, dioxane, N-methylpyrrolidone (NMP) or combinations of any two or more of the foregoing. Exemplary combinations include, but are not limited to acetic acid/xylene, benzene/acetic acid, xylene/acetic acid/acetic anhydride, toluene/acetic acid, n-heptane/acetic acid, dimethyl ketone/acetic acid, ethylmethyl ketone/acetic acid, acetonitrile/acetic acid and the like, wherein the acetic acid is preferably glacial acetic acid. Two-phased solvent systems, such as n-heptane/glacial acetic acid and xylene/glacial acetic acid seem somewhat more difficult to filter than one-phase solvent systems, such as toluene/glacial acetic acid.

It is to be appreciated that improved processes for the production of the methylidene malonates according to the present invention may further comprise any number of additional steps whereby the malonate reactant or precursor is subjected to one or more additional reactions by which one or both of the ester groups of the malonate or precursor is removed, replaced, and/or modified. For example, one or both ester groups could be replaced with a higher carbon number hydrocarbyl group, with a hydrocarbyl group different from the other, with a heteroatom or heteroatom-containing group, moiety or radical, and the like. With respect to the latter, for example, one or both ester groups could be modified to include an ether, ester, aldehyde, ketone, cyano, aryl, halo or epoxide group. Further, such groups or moieties could be functional or reactive groups or moieties for subsequent cross-linking and/or co-polymerization of the methylidene malonates with itself or, preferably, with other monomers, compounds, reactants, cross-linkers, hardeners, etc.

According to a first embodiment of the present invention there is provided an improved adduct-free process for the production of methylidene malonates wherein the improvement comprises the addition of a reaction phase stabilizer system comprising one or more primary anionic polymerization inhibitors, at least one of which must be a liquid phase anionic polymerization inhibitor, most preferably an strong acid, especially a mineral, organic or sulfonic acid, alone or in combination with at least one free radical polymerization inhibitor, to the reaction mix and/or the crude reaction product, wherein, in the latter case, the stabilizer system is added just prior to, concurrent with or following completion of the formation of the methylidene malonate. The reaction phase stabilizer system may also comprise, as an optional constituent, one or more secondary anionic polymerization inhibitors, as defined below.

If the reaction phase stabilizer is to be added to the reaction mix prior to or during the condensation reaction, particularly before substantial completion thereof, it is important to ensure that the anionic polymerization inhibitor or the amount of its addition will not detrimentally affect the condensation reaction, i.e., the formation of the methylidene malonate, or at least has a minimal effect on the reaction. In particular, where the catalyst is a basic catalyst, it is important that the anionic stabilizer not to neutralize the catalyst as this may have a detrimental impact on the catalyst and/or interfere with the reaction: thereby reducing if not precluding, the efficacy thereof. Similarly, when the reaction phase stabilizer system comprises both the anionic polymerization inhibitor and the free radical polymerization inhibitor, it is preferred that the latter not be added to the reaction mix prior to or during the reaction, at least no until the reaction is substantially complete.

Preferably, the reaction phase stabilizer system is added to the crude reaction product concurrent with or, more preferably, immediately following removal of the solids components contained therein, e.g., catalyst, and/or washing of the crude reaction product, but prior to fractionation. In any event, the reaction phase stabilizer system should be added to the crude reaction product or, if appropriate, the crude liquid reaction product, prior to storing the same or prior to subjecting the same to any further process steps, including fractionation steps, that involve heat and/or long periods of standing, even at room temperature.

In those instances wherein the reaction phase stabilizer system comprises a plurality of polymerization inhibitors, e.g., a plurality of anionic polymerization inhibitors and/or combinations of anionic polymerization and free radical polymerization inhibitor(s), it is preferred, though not necessary, that all of the inhibitors be added at the same time or generally in the same phase of the reaction process, more preferably following completion of the reaction and, most preferably, following removal of the solids from the crude reaction process. Nevertheless, it is also contemplated that one or more components of the reaction phase stabilizer may be added at a different time or stage of the reaction process than the other components or that a portion of one component or of any or all components may be added at one stage of the process and the remainder at another. For example, as noted above, where both an anionic polymerization inhibitor and a free radical polymerization inhibitor are used, the former may be added to the reaction mix prior to or during the reaction for the production of the methylidene malonates and the latter to the crude reaction product or, preferably, to the crude liquid reaction product.

In those instances where one or more components of the reaction phase stabilizer system is added to the reaction mix prior to or during the reaction or is added to the crude reaction product prior to the removal of the solids and/or prior to completing the washing of the crude reaction product or crude liquid reaction product, it may be necessary, and most likely will be necessary, or at least beneficial, to add an additional quantity of the reaction phase stabilizer system, or the particular component thereof that was previously added, to the crude reaction product or crude liquid reaction product, as appropriate, to make up for any lost material and ensure process and product stability.

As noted above, the reaction phase stabilizer system must have at least one liquid phase anionic polymerization inhibitor; however, concern also exists for instability in the vapor phase. This may be addressed by employing an anionic polymerization inhibitor that is capable of acting as both a liquid phase and a vapor phase stabilizer. Alternatively, one can employ a separate vapor phase anionic polymerization inhibitor or a secondary anionic polymerization inhibitor that is either a vapor phase stabilizer or a dual liquid-vapor phase stabilizer.

According to a second aspect of the present invention, there is provided an improved process for the separation, purification, and isolation, i.e., the fractionation, of methylidene malonates from the crude reaction product or crude liquid reaction product produced in an adduct-free process, wherein the improvement comprises the addition of a separation phase stabilizer system to the recovered fractions, i.e., the separated or purified methylidene malonate material. Like the reaction phase stabilizer system, the separation phase stabilizer system comprises one or more anionic polymerization inhibitors, at least one of which must be a liquid phase anionic polymerization inhibitor, alone or in combination with at least one free radical polymerization inhibitor. However, unlike the reaction phase stabilizer system, the anionic polymerization inhibitor(s) of the separation phase stabilizer system may be just secondary anionic polymerization inhibitors. Additionally, in those situations where the fractionation process is merely a continuation of the reaction process discussed above, one may optionally employ the reaction phase stabilizer system as the separation phase stabilizer system. Generally, though, the reaction phase stabilizer system and the separation phase stabilizer system will be different.

Following on the foregoing, it is also to be appreciated that a given process may involve different separation phase stabilizers during the full course of the separation, purification and recovery steps. For example, while one separation phase stabilizer system may be employed for each distillation step or a multi-step distillation, a different separation phase stabilizer may be used in the final, purified products (and hence its collection vessel if pre-treated).

The improved separation process of the present invention may be applied to any of the known processes for the fractionation or separation, purification and recovery of methylidene malonates. Such methodologies include: distillation (including fractional distillation), flash distillation, solvent stripping, crystallization, precipitation, extraction, gel filtration, electrophoresis, foam fractionation, electromagnetic separation, evaporation (including thin film evaporation), press extraction, and various forms of chromatography as well as combinations of the foregoing. The improved separation process is especially beneficial for fractionation distillation and flash distillation as shown in the examples below. For convenience, the following discussion will be made with respect to distillation, notably fractional distillation; though it is to be appreciated that those skilled in the art will readily appreciate the modifications and variations that will be needed to adopt the process to the other fractionation methods, including flash distillation.

Furthermore, as noted above, the improved separation process may be applied to the stabilized crude reaction product or crude liquid reaction product of the improved reaction process described above. From a commercial perspective, it is preferred that it be adopted as a continuation of that process; although, it can also be applied to those products following storage of the same. More importantly, it is to be appreciated that this improved separation process is also applicable to the fractionation of crude reaction products and crude liquid reaction products resulting from other known methods for the production of methylidene malonates. For example, it may be applied to those unstabilized or alternatively stabilized crude methylidene malonate products resulting from any of the adduct-free methods known in the art, as mentioned above and in the background section.

Where the crude product to be subjected to the improved separation process of the present invention is not stabilized, then one should first add a separation phase stabilizer system to the crude products before commencing fractionation. This separation phase stabilizer system may be the same or different from the separation phase stabilizer system to be added to the recovered fractions. Similarly, even if the crude product to be subjected to fractionation contained an alternate stabilizer or stabilizer system, one may consider supplementing, and preferably will supplement, the stabilization of the crude product with an amount of the separation phase stabilizer system.

While the separation phase stabilizer system may be added to the recovered material during or following its collection, it is preferred that at least a portion of the separation phase stabilizer system be added to the collection flask or vessel prior to initiating fractionation or at least prior to collection of the fraction to be recovered and the remainder added following completion of the fractionation or, as appropriate, collection of the given fraction(s). In the case of flash distillation, it is also preferred to add a portion of the separation phase stabilizer system to the still pot or vessel in which the vapor is to be formed. The amount of the separation phase stabilizer system to be added to the empty collection flask or vessel will be based on the projected amount of material to be collected: generally the amount will be somewhat less than that needed if the full amount projected were to actually be recovered. Once the fractionation is completed, the level of separation phase stabilizer will then be adjusted upward, as appropriate, based on the actual amount collected. And, as with the reaction phase stabilizer system when added to the crude liquid reaction product, it is preferred, though not required, that all components of the separation phase stabilizer system be added concurrently or nearly so. The exception, of course, is where a vapor phase stabilizer is to be continuously introduced to the fractionation apparatus, as further described below.

The process as described above, i.e., the addition of the separation phase stabilizer system, will be used for each successive fractionation process and/or fractionation step employed. For example, in fractional distillation, if a given fraction or combination of fractions is to be redistilled, the fractions collected during the redistillation will also be stabilized with the separation phase stabilizer.

In the practice of the preferred embodiment of this aspect of the present invention, it is most convenient to place a quantity of a stock solution of the separation phase stabilizer system, or one or more components thereof, especially, the anionic polymerization, in the collection vessel or container, allow the solution to evenly coat the inner surface of the collection vessel or container and then pour out the excess. Since the solvent for the stock solution is typically a volatile solvent, e.g., toluene, ethanol, acetone, etc., or a copolymerizable or an inert monomer, e.g., an acetate or acrylate, the container or vessel is promptly attached to the fractionation apparatus or sealed to prevent loss of the stabilizer solution until the container or vessel is to be attached to the fractionation apparatus. On the other hand, so long as the loss of solvent will not affect the inhibitors in the vessel, which essentially coat the inside wall of the vessel, one may allow some or all of the solvent to evaporate before sealing to protect the remaining inhibitors. One can calculate the amount of inhibitor(s) left in the container or vessel by weighing the weight gain. Then, once the separation process is completed and the collected sample sealed in the container, the container is then again weighed and the proper weight of the recovered material determined so that one can then determine the amount of stabilizer to be added to bring the total stabilizer content to the appropriate level.

Depending upon the nature of the fractionation process employed, it is preferred to include one or more vapor phase or dual liquid-vapor phase anionic polymerization inhibitors in the separation phase stabilizer system. This is particularly so for those fractionation processes which involve the formation of a vapor of or containing the methylidene malonate. If the system is a closed or sealed system, then one only need add the vapor phase stabilizer with the liquid phase stabilizer. However, if it is an open system or a system under a drawn vacuum, then it is necessary to supply a continuous feed of the vapor phase stabilizer to maintain a given level of the stabilizer in the vapor phase or the airspace of the apparatus. For example, in a traditional distillation apparatus, especially one that is under vacuum, it is preferred to bubble a constant vapor of the vapor or dual liquid-vapor phase polymerization inhibitor through the system.

The adoption of either or both of the improved reaction and separation processes described above results in a marked stability to the overall process, thereby enabling consistent and more predictable results. In addition to the enhanced stability and, hence, predictability achieved by the use of the stabilizer systems, their use also results in still higher yields of greater purity, particularly as compared to the performance of similar processes conducted in the absence of polymerization inhibitors or with other stabilizers. Not intending to be bound by theory, it is believed that the high temperatures of the purification processes, especially in flash distillation, may be cracking dimers, trimmers, oligomers and polymers that have formed in the reaction step, leading to more monomer production with the stabilizers preventing their reformation.

By implementing the improved processes as set forth herein, one realizes more consistent and improved yields. For example, one may attain crude yields in excess of 25%, preferably in excess of 35%, more preferably in excess of 40%, most preferably in excess of 50% or more, on a consistent and repeatable basis. Most importantly, these yields are attained with a concomitant high purity, generally 60% or more, preferably 75% or more, more preferably 80% or more, most preferably 90% or more. More importantly, the further fractionation of these yields by the improved separation process and associated separation phase stabilizer system results in even higher purities with excellent yields. Generally, one is able to realize purified yields in excess of 20%, preferably in excess of 30%, more preferably in excess of 35%, most preferably of about 40% or more, based on the original malonate reactant, on a repeatable and consistent basis. Furthermore, these "purified" fractions or collections of methylidene malonate generally have purities exceeding 80%, preferably 85%, more preferably 90%, most preferably 95%. Thus, even if the yields, especially the purified yields, slip below the aforementioned targets, the loss in yield is more than made up for by the increased purity attained with the improved processes. Hence; yields as low as 15%, even 10%, with high purity of 85% or higher, preferably 90% or higher, most preferably 95% or higher, provides a suitable process and is within the scope of the present invention. Generally speaking, the improved processes of the present invention provide for high purity wherein the purified product contains less than 8%, preferably less than 6%, most preferably less than 4%, of impurities and less than 12%, preferably less than 10%, most preferably less than 8% of the analogs of the desired product, on a consistent basis.

Thus, while there may be, and most likely is, some loss in overall yield as a result of the fractionation process, especially if multiple fractionation processes are employed or the same process is repeated one or more times, the purity of the product significantly improves. This is especially important from a commercial perspective as the purity of the methylidene malonate is critical to and correlates with its utility and performance. Specifically, as discussed in Coover et. al. (U.S. Pat. No. 3,221,745) and as found by Applicants, even minor amounts of impurities impair their utility, especially the cure or polymerization characteristics of these monomers. Concern with the presence and amount of impurities and byproducts is even more paramount, if not an absolute use limiting factor, in the case of methylidene malonates intended for medical applications, especially skin bonding applications, e.g., skin bonding adhesives, or other applications that may require its use in the human body.

Having generally described the use and application of the stabilizer systems and the improved processes employing the same, attention now is drawn to the two stabilizer systems and their respective constituents.

The reaction phase stabilizer system comprises at least one anionic polymerization inhibitor (also referred to as the primary anionic polymerization inhibitor), at least one of which is a liquid phase anionic polymerization inhibitor, alone or in combination with at least one inhibitor of free radical polymerization. Preferably the primary anionic polymerization inhibitor(s) is an acid, especially a mineral acid, an organic acid, or a sulfonic acid. Especially suitable anionic polymerization inhibitors are characterized as being strong acids, most preferably very strong acids. As used herein, a strong acid is an acid that has an aqueous pKa at room temperature of about 2.0 or less and a very strong acid is one having an aqueous pKa of about 1.0 or less. Strong acids include, but are not limited to, strong mineral acids and strong organic acids including maleic acid, difluoroacetic acid, dichloroacetic acid, and picric acid. The very strong acids include, but are not limited to, the very strong mineral and/or oxygenated acids as well as the sulfonic acids. By way of example, but not limitation, exemplary very strong acids include sulfuric acid, nitric acid, perchloric acid, trifuoroacetic acid, trichloroacetic acid, hydrochloric acid, hydrobromic acid, benzene sulfonic acid, methane sulfonic acid, trifluoromethane sulfonic acid, fluorosulfonic acid, chlorosulfonic acid, paratoluene sulfonic acid, and the like. Preferably the primary anionic polymerization inhibitor is selected from trifluoroacetic acid, sulfuric acid, maleic acid, perchloric acid and chlorosulfonic acid; most preferably sulfuric acid, maleic acid, and/or trifluoroacetic acid. In part, the selection of the stabilizer is temperature dependent. For example, it was found that the lower temperatures of the present direct process favors maleic acid as the reaction phase stabilizer over sulfuric acid. The latter, though, is preferred over the maleic acid when adding to the isolated product.

With certain exceptions, it is preferred that the individual polymerization inhibitors making up the reaction phase stabilizer system are not readily vaporized or otherwise drawn or removed from the crude reaction product or crude liquid reaction process on standing or under the selected fractionation technique to be employed for the separation and recovery of the purified methylidene malonate. This is especially important in high temperature separation steps such as distillation, particularly fractional distillation. While the passing over of small amounts of the anionic polymerization inhibitor may be tolerated and acceptable, it is generally preferred that no or negligible amounts pass over so as to avoid the happenstance that the crude reaction product becomes deficient in the amount of stabilizer present before separation is completed. A deficiency in the level of the stabilizers will lead to a general instability of the reaction product which, in turn can lead to an undesirable and untimely formation of oligomers and/or polymers of the methylidene malonate and/or the formation of other byproducts and degradation products, especially glutarates: all of which will reduce significantly the yield of recovered material in the collection vessel.

The first exception is where the anionic stabilizer is employed in a sufficient excess to account for the loss or passing over of the stabilizer in the vapor phase.

The second exception to the foregoing is polymerization inhibitors that distill over slowly so as to remain in sufficient quantities in the crude reaction product or crude liquid reaction product so as to prevent its premature polymerization prior to completion or substantial completion of the separation process. These inhibitors have the added benefit of serving as a stabilizer of the vapor phase as it traverses to the collection flask. Thus, for the purpose of this application and the appended claims, dual functional liquid-vapor phase anionic polymerization inhibitors are to be deemed liquid phase anionic polymerization inhibitors: thereby satisfying the need for the at least one liquid phase anionic polymerization inhibitor. An example of an anionic polymerization inhibitor capable of acting as both a liquid phase and vapor phase stabilizer is trifluoroacetic acid. When such dual functional anionic polymerization inhibitors are used, it may be desirable to add a bit more of the inhibitor to the reaction vessel so as to account for the loss during the separation step.

Another exception is where the reaction phase stabilizer system further comprises a secondary anionic polymerization inhibitor that is or has the capacity to act as a vapor phase polymerization inhibitor or as a dual vapor-liquid phase polymerization inhibitor. As discussed in greater detail below, such secondary vapor phase and dual liquid-vapor phase anionic polymerization inhibitors include sulfur dioxide ($SO_2$), boron trifluoride ($BF_3$), nitric oxide (NO) or hydrogen fluoride (HF).

Generally speaking, the amount of the primary anionic polymerization inhibitor to be employed during the reaction phase should be from about 1 ppm to about 10,000 ppm, more specifically, from about 5 ppm to about 6,000 ppm based on the weight of the malonate or precursor thereof. Of course, the specific amount will vary depending upon the strength of the anionic polymerization inhibitor: in the case of an acid, the pKa value. Generally, it appears that the stronger the polymerization inhibitor, the lesser the quantity of anionic polymerization inhibitor needed. For example, a strongly acidic anionic polymerization inhibitor like sulfuric acid may be used in quantities in the lower end of the range, e.g., from about 1 to about 2000, preferably from about 5 to about 500, more preferably from about 10 to about 200 ppm, most preferably from about 10 to about 100 ppm. On the other hand, a comparatively weaker acid, like maleic acid, will be used towards the higher end of the range, generally from about 100 to about 5000, preferably from about 500 to about 4500, more preferably from about 1000 to about 4000, most preferably from about 2500 to about 3500 ppm based on the amount of the malonic acid ester or precursor thereof. Generally, the amount of anionic polymerization inhibitor to use can be determined by simple experimentation.

As indicated above, the reaction phase stabilizer system may also comprise, as an option, one or more secondary anionic polymerization inhibitors. These are generally anionic polymerization inhibitors that, on their own, do not appear to perform well as the sole reaction phase anionic polymerization inhibitor, but which, when combined with the latter, provide an additive or synergistic stabilization effect to the overall crude product and reaction system. Suitable secondary anionic polymerization inhibitors include liquid phase, vapor phase, and dual liquid-vapor phase anionic polymerization inhibitors. Generally, secondary anionic polymerization inhibitors are also acids, especially, but not exclusively, those having an aqueous pKa of more than 2, more commonly more than 3, and/or having low conductivity in the non-aqueous medium. Exemplary secondary anionic polymerization inhibitors include, but are not limited to phosphoric acid; phosphorus pentoxide ($P_2O_5$); organic acids such as acetic acid, benzoic acid, fumaric acid, chloroacetic acid, cyanoacetic acid and mixtures thereof, especially acetic acid, benzoic acid or mixtures thereof; sulfur dioxide; nitric oxide; boron trifluoride; and hydrogen fluoride; as well as combinations of any two or more of the foregoing. As mentioned above, certain of these secondary anionic polymerization inhibitors, including sulfur dioxide, nitric oxide, boron trifluoride, and hydrogen fluoride, are or are also capable of acting as vapor phase anionic polymerization inhibitors. Additional exemplary secondary anionic polymerization inhibitors, including vapor phase inhibitors, and mixtures thereof are set forth in Malofsky et. al., U.S. Pat. No. 6,512,023 B1, which is hereby incorporated herein in its entirety by reference.

The amount of the secondary anionic polymerization inhibitor to be employed, if present, will vary depending upon the strength of the same in inhibiting anionic polymerization and the nature of the stabilizer used. For example, the secondary anionic polymerization inhibitors will generally be employed at a level of from about 1 to about 500 ppm, preferably from about 10 to about 400 ppm, most preferably from about 15 to about 200 ppm. As with the primary anionic polymerization inhibitors discussed above, the strength of the inhibitor will also affect its level of use. For example, for the weaker acids such as acetic or benzoic acid, 25 to 400 ppm may be more appropriate whereas lesser amounts, such as from about 5 to about 200 ppm, preferably from about 15 to about 100 ppm will suffice for the stronger acids such as phosphoric acid. Similarly, when a vapor phase secondary anionic polymerization inhibitor is present, it will generally be employed at a level of from 1 to about 500 ppm, preferably from about 5 to about 200 ppm, more preferably from about 10 to about 100 ppm. For purposes of clarification, the amount of the secondary anionic polymerization inhibitor, when present, is in addition to the amount of the primary anionic polymerization inhibitor mentioned above.

As mentioned above, the reaction phase stabilizer system employed in the improved processes of the present invention may also include, and preferably does include, one or more free radical polymerization inhibitors. Suitable free radical inhibitors include, but are not limited to, the quinones and hindered phenols, especially the hydroquinones, hydroquinone monomethyl ether, catechol, pyrogallol, benzoquinones, 2-hydroxy benzoquinones, p-methoxy phenol, t-butyl catechol, butylated hydroxy anisole (BHA), butylated hydroxy toluene (BHT), t-butyl hydroquinones, 2,2"-methylene-bis (6-tertbutyl-4-methylephenol), and mixtures thereof. Generally speaking the amount of free radical inhibitor to be added to the system should be from about 100 to about 20,000, preferably from about 300 to about 10,000, more preferably from about 500 to about 5000 ppm, most preferably from about 800 to about 2000 ppm, based on the amount of malonic acid ester or, as appropriate, the malonate precursor. Generally, the optimal amount of free radical polymerization inhibitor to use for the particular system can be determined by simple experimentation.

Of course, a number of process variables may affect the amount and selection of the specific inhibitors to be employed in the reaction phase stabilizer system and are to be considered when formulating the stabilizer system. Process variables such as the reaction medium, the temperature at which the reaction is run, the reactants, the intended products, as well as the byproducts typically formed, can all affect the performance and selection of the various stabilizer(s) making up the reaction phase stabilizer system. For example, reaction processes employing or encountering higher temperatures seem to favor the stronger acids, like sulfuric acid; whereas, lower temperature processes seem to favor the comparatively weaker acids, like maleic acid.

Perhaps one of the most important variables affecting performance is the degree of dissociation of the selected polymerization inhibitors in the reaction medium, especially non-aqueous based reaction media. In this respect, it is particularly important, if not paramount, that sufficient dissociation of the inhibitors, especially the primary anionic polymerization inhibitors, take place to manifest a sufficient degree of the acid effect on polymerization inhibition. As discussed in Malofsky et. al. (U.S. Pat. No. 6,512,023), one may determine the degree of dissociation empirically by measuring the conductivity of the medium into which the acid is added in order to assess sufficient dissociation: a higher conductivity being evidence of a greater degree of dissociation.

Where the degree of dissociation in a particular medium or reaction mix is of concern, one may enhance dissociation or overcome this issue by forming stock solutions of one or more of the selected polymerization inhibitors wherein the inhibitors are first dissociated or dissolved in a favorable media or solvent before being added to the reaction mix or crude reaction product. Those skilled in the art will readily recognize suitable media and solvents for a given inhibitor or inhibitor combination as well as compatible media or solvents for the given reaction media or reactant mix. This can also be determined by simple experimentation. Exemplary media or solvents for forming such stock solutions are cyanoacetic acid, toluene and a combination thereof.

As discussed above, the present invention also provides for an improved process for the separation, purification and recovery, i.e., fractionation, of methylidene malonate wherein the improvement comprises the use of a second stabilizer system, the separation phase stabilizer system, during the fractionation process(es). The separation phase stabilizer system comprises one or more primary anionic polymerization inhibitors, one or more secondary polymerization inhibitors, or a combination of the two, alone or in further combination with one or more free radical polymerization inhibitors, all as described above with respect to the components of the reaction phase stabilizer system. Indeed, while not necessary, it is to be appreciated that the separation phase stabilizer system may be the very same stabilizer system as the reaction phase stabilizer system. Similarly, except as noted below with respect to a vapor or dual liquid-vapor phase stabilizer, the amounts by which the individual polymerization inhibitors of the separation phase polymerization inhibitors are used is also consistent with that of the reaction phase stabilizer systems; though the tendency may be that their use is towards the middle and lower end of the ranges specified above so as not to subsequently affect the cure or polymerization characteristics of the purified monomer. Here, however, it is to be remembered that the amount is based upon the amount of methylidene malonate product expected and/or actually recovered from the separation process, not the malonate precursor material. Additionally, where the sole anionic polymerization inhibitor of the separation phase stabilizer system is a secondary anionic polymerization inhibitor, the amount to be employed will be consistent with the amount which would have been used if it were a primary anionic polymerization inhibitor as opposed to the lesser amounts used when a secondary anionic polymerization inhibitor is used to supplement the primary anionic polymerization inhibitor as set forth above.

When used, the amount of vapor phase or dual liquid-vapor phase anionic polymerization inhibitor to be employed in the improved fractionation process will vary depending upon the nature of the fractionation process itself. If the fractionation process is conducted in a closed system, one where there is no flow of air or other gas in or through the fractionation apparatus, or the collected volume is to be stored, whether as monomer or formulated material, then the vapor phase inhibitor will generally be employed at a level of from 1 to about 500 ppm, preferably from about 5 to about 200 ppm, more preferably from about 10 to about 100 ppm. However, where the fractionation process is conducted in an open system or under vacuum, one must account for the loss of the vapor phase stabilizer. Hence, in those processes, it is preferred to continuously introduce vapor phase stabilizer to the given system or apparatus, e.g., by bubbling, in order to maintain a concentration consistent with the levels mentioned for the closes systems. As note above, suitable vapor phase and dual liquid-vapor phase stabilizers include, trifuoroacetic acid, sulfur dioxide, boron trifluoride and hydrogen fluoride. Of course, the vapor phase stabilizer may be added to the liquid component as well as bubbled in, especially where the stabilizer is a dual liquid-vapor phase stabilizer.

As known in the art, the methylidene malonates formed by the improved process of the present invention may be employed in a number of organic syntheses and polymer chemistry applications. In particular, they are especially useful in the preparation of various adhesive and sealant applications including industrial, commercial and consumer adhesive and sealant applications as well as in skin bonding applications for human and animal skin bonding.

Having described the invention in general terms, Applicants now turn to the following examples in which specific combinations of reactants, solvents and stabilizers as well as varied reaction times were evaluated. These examples are presented as demonstrating the surprising attributes of the improved processes of the present invention as well as the unexpected synergy resulting from the use of the combination of the anionic and free radical polymerization inhibitors. These examples are merely illustrative of the invention and are not to be deemed limiting thereof. Those skilled in the art will recognize many variations that are within the spirit of the invention and scope of the claims.

EXAMPLES

Examples 1-12 and Comparative Examples CE1 and CE2—Direct Process

The direct process for the production of methylidene malonates is one that does not employ an intermediate diene or polynuclear aromatic adduct. Unless otherwise indicated, the following apparatus and process steps were employed.

A suitably sized reaction vessel having a three neck reactor head in a heating mantle with a variable power source was employed. The vessel was equipped with a motorized paddle blade for mixing the reactants in the vessel. The vessel also included appropriately placed thermometers/thermocouples and a Dean-Starke trap with condenser.

The reactor was then charged with the catalyst, the formaldehyde source (paraformaldehyde 97%, unless otherwise stated), glacial acetic acid (>80% acid by wt.) and an azeotropic solvent (typically xylene, n-heptane, toluene or n-butyl acetate).

The contents of the vessel were then heated, generally to about 50° C., and then the malonate, with or without the reaction phase stabilizer system, was added slowly over time with continued, gradual heating and stirring until an exotherm is noted. Depending upon the azeotropic solvent, this may occur once the pot temperature reaches about 105° C. Shortly after the exotherm, water will begin to form and condense in the reflux separator. The amount of water collected will vary depending upon the catalyst and acetic acid employed; however, with copper hydrate and acetic acid, one will typically collect 1.5 to 2 times the theoretical amount of water. The water is removed and discarded and the reaction is allowed to continue until a reflux head temperature equal to the boiling point of the pure azeotrope solvent. Thereafter, the reactor contents are allowed to cool to less than 30° C.

Following cooling, the reaction mix was then filtered through a #2 fluted Whatman filer paper to isolate the crude liquid reaction product. Oftentimes, particularly if a two-phase solvent system was used, MeCl$_2$ was used to rinse the reactor and wash the filtrate (2×100 ml). Unfortunately, this process results in a considerable loss of crude liquid reaction product due to capillary action of the paper as well as materials trapped in or on the catalyst solids. Other filtration methods, such as a Buchner funnel with vacuum filtration, may be a more efficient separation method. If not already present in the malonate, the reaction phase stabilizer system was then added to the filtrate, the crude liquid reaction product, either prior to or following a solvent strip to remove the solvent and MeCl$_2$.

In those examples where sufficient filtrate was obtained, the filtrate was subjected to solvent stripping prior to performing a crude distillation. Solvent strip was initially conducted at atmospheric pressure. Thereafter, to remove any remaining solvents and/or gases, the system is then subjected to a vacuum stripping. After a system vacuum of ~0.5 mmHg is maintained and the solvent strip completed, the trap is cleared and the collection vessel replaced with a clean vessel. During the vacuum strip, the temperature of the reactor contents is not allowed to exceed 55° C. so as to prevent the boiling of the methylidene malonate monomer.

Following stripping, the filtrate was then subjected to distillation. The distillation apparatus comprised an appropriately sized glass round bottomed flask/reactor equipped with a magnetic stirring bar, a heating mantle, a distillation head and condenser, thermometer, vacuum claisen adapter, and collector vessel. To protect the vacuum source from plugging, liquid nitrogen in a Dewar flask with a double glass trap was employed. The stabilized filtrate together with 2-3 PTFE boiling chips were then placed into the flask and distillation initiated.

In an effort to isolate purer materials, the collected product from the crude distillation were then subjected to one or more additional fractional distillations and the fractions collected. The same apparatus is used with the exception that an 8" de-entrainment column equipped with ~3" of stainless steel packing is fitted between the distillation head and the distillation flask. Additionally, a cow receiver was used to facilitate fractionation. Here, the collection flasks were typically pre-treated with the separation phase stabilizer system.

In certain instances, in order to increase the efficiency of the process and cost effectiveness, the crude yields of multiple processes were combined and a composite distillation conducted. For example, Examples 2, 3, 4 and 5 were combined and then subjected to fractional distillation and produced a 76.6% yield.

The specific reactant systems evaluated and the results attained therewith are set forth in Table 1. In Table 1 DEM is diethylmalonate, PF is paraformaldehyde (97%), GAC is glacial acetic acid, MA is maleic acid, HQ is hydroquinone and SA is sulfuric acid.

As evident from the results presented in Table 1, the use of the reaction phase stabilizer system provided enhanced performance and yields as compared to those without the reaction phase stabilizer system. It is to be appreciated that these yields are not necessarily indicative of the methylidene malonate as it has been found that these reactions produce a number of isomers and related species, including dimer, trimer, and oligomers as well as some polymer chains, as well as certain undesired byproducts including glutarates and/or acetates.

| Example | $Cu(OAc)_2$ | Solvent Amt. (ml) | PF | DEM | GAC | MA | HQ | SA | Crude Dist. Yld (g) | Reaction time (hrs) | Notes |
|---|---|---|---|---|---|---|---|---|---|---|---|
| E1 | 33.8 | X 400 | 38 | 108 | 71 | — | 0.324 | 0.324 | 67.03 | 4 | HQ/SA added to DEM prior to reaction, $MeCl_2$ wash |
| E2 | 3.4 | X 200 | 38 | 108 | 35.5 | — | 0.324 | 0.324 | 45.82 | 3 | HQ/SA added to DEM prior to reaction, $MeCl_2$ wash |
| CE1 | — | X 200 | 38 | 108 | 35.5 | — | 0.324 | 0.324 | — | 2.5 | No reaction |
| E3 | 33.8 | X 400 | 38 | 108 | 71 | — | — | — | — | 3.5 | Crude yield stabilized to 5 ppm HQ and |
| E4 | 19.4 | H 300 | 46.4 | 242.7 | — | — | 0.14 | 0.14 | 73.77 | 3.25 | $SO_2$ HQ/SA added after filtering before solvent strip, crude distillate subject to second distillation with 2.63 g of 1000 ppm SA and $SO_2$ stock solution in cyanoacetate added to collection flask prior to distillation |
| E5 | 19.4 | H 250 | 46.4 | 161.8 | — | — | 0.14 | 0.14 | 53.35 | 2.75 | HQ/SA added after filtering before solvent strip, crude distillate stabilized to 5 ppm SA and $SO_2$ using stock solutions |
| E6 | 19.4 | H 200 | 34 | 161.8 | — | — | * | * | 51.82 | 3 | Filtrate stabilized to 3000 ppm HQ and SA (based on CHO) and stabilized filtrate and 100 ml Tricresyl phosphate added to flask for distillation |
| CE2 | 33.8 | X 400 | 38 | 161.8 | 71 | — | — | — | 36.52 | 3 | 20 g $P_2O_5$ added to filtrate after filtering, $MeCl_2$ wash |
| E7 | 33.8 | X 400 | 38 | 161.8 | 71 | — | 0.52 | — | 69.62 | 2.75 | HQ and 20 g $P_2O_5$ added to filtrate after filtering, $MeCl_2$ wash |
| E8 | 33.8 | X 400 | 38 | 161.8 | 71 | 0.87 | 0.87 | — | 70.66 | 3 | MA and HQ added to filtrate after filtering, $MeCl_2$ wash |
| E9 | 33.8 | H 400 | 38 | 161.8 | 71 | 0.87 | 0.87 | — | 121.68 | 1.5 | MA and HQ added to filtrate after filtering |
| E10 | 33.8 | H 400 | 38 | 161.8 | 71 | 0.87 | 0.87 | — | 119.31 | 2 | MA and HQ added to filtrate after filtering |
| E11 | 33.8 | H 400 | 38 | 161.8 | 71 | 0.87 | 0.87 | — | 127.68 | 2 | MA and HQ added to filtrate after filtering |
| E12 | 33.8 | T 400 | 38 | 161.8 | 71 | 0.87 | 0.87 | — | 136.69 | 3.5 | MA and HQ added to filtrate after filtering |
| E13 | 33.8 | T 400 | 38 | 161.8 | 71 | 0.87 | 0.87 | — | 154.02 | | MA and HQ added to filtrate after filtering |

Solvents - H - heptane; X - p-xylene; T - toluene

Example 13

135.2 g copper acetate hydrate, 1,281.36 g diethyl malonate, 247.1 g paraformaldehyde (97%), and 284 g glacial acetic acid were charged to a round bottom reactor. The reactant mix was gradually heated and allowed to react for a period of 3.75 hours and allowed to cool. The reaction mix was then filtered with a Vacfilter through #2 Whatman paper. 1472 grams of the filtrate were then charged to a distillation flask. Approximately 95 g of solvent was recovered in a liquid nitrogen trap during the filtering step. The resultant crude product was then stabilized with 4.96 g maleic acid (MA) and 4.96 g hydroquinone (HQ) before solvent stripping and crude distillation. The material was stored in a refrigerator (2-8° C.) for several days.

The crude product was then returned to room temperature and filtered under vacuum filtering with a 1/8 inch bed of diatomaceous earth on #541 Whatman paper. This filtrate was then up-stabilized with 2.59 g. of maleic acid and 2.59 g of hydroquinone and charged to a distillation flask. This material was subject to condensation distillation and then fractional distillation. Two primary fractions were obtained as follows: Fraction 1—1$^{st}$ cut upon distillation (70.21 g) and Fraction 2—the main fraction (627.99 g-45.64% yield) with 418.24 g remaining as pot residue.

621.1 g of Fraction 2 was then up-stabilized with 12.1 ppm sulfuric acid and 1000 ppm hydroquinone and then subjected to a further fractional distillation. This yielded five fractions, plus the still bottoms (101.28 g) and 11.64 g of material collected in the trap condenser. These fractions were each stabilized with 15 ppm trifluoroacetic acid and 1000 ppm hydroquinone. Mass Spec and GC analysis indicated the presence of a high level of unsaturation which is believed to be indicative of the presence of methylidene malonate species.

Example 14

15.7 g copper acetate hydrate, 750 g 2.1.2 malonate, 131.09 g paraformaldehyde (97%), and 230.74 g glacial acetic acid and 800 ml toluene were charged to a 2 L 3-necked flask equipped with a Dean-Stark trap with a heating mantle magnetic stirrer. The reactant mix was gradually heated and allowed to react for a period of 3.5 hours during which 125 ml of water were removed via the Dean-Stark trap at gentle reflux. 1000 ml toluene was added and wash with 5×500 ml 0.05N aqueous sulfuric acid portions. Following washing, the reaction product was stabilized to 15 ppm sulfuric acid and 1000 ppm hydroquinone. The crude product was then subjected to solvent strip by rotary evaporation at 100 mmHg with a gradual rise in vacuum to 6 mm Hg in an 80° C. bath. This yielded 741.7 g crude product (94%).

The crude product was then subject to flash distillation wherein half of the crude product was added to a dry still pot in a 210° C. oil bath, the still pot containing 6.0 g of 0.1% sulfuric acid solution and 0.6 g hydroquinone, via a pressure equalizing funnel at a rate of approximately 4 drops per second. The product was collected as a colorless liquid at 115-125° C. at 1.5-2.5 mmHg. The same process was repeated for the second half of the crude product. A total of 289 g of product (37% yield) was recovered and stabilized to 15 ppm sulfuric acid and 1000 ppm hydroquinone.

The stabilized product was then subjected to fractional distillation which yielded the following:
Fraction 1—35-50° C. @ 1.5 mmHg—yield 32.68 g
Fraction 2—70-95° C. @ 1.1 mmHg—yield 7.58 g
Fraction 3—97-105° C. @ 0.8 mmHg—yield 7.58 g
Fraction 4—remove fractionating column, 90-95° C. @ 0.4 mmHg—yield 8.04 g which gave a 5 second fixture time on glass slides.

Fraction 3 was then subjected to a second fractional distillation. The fraction was further up-stabilized with 15 ppm sulfuric acid and 1000 ppm hydroquinone, degassed and then fractionally distilled. This fraction provided four sub-fractions (3-1, 3-2, 3-3 and 3-4), each of which were stabilized with 15 ppm trifluoroacetic acid and 1000 ppm hydroquinone, of 26.25, 53.44, 54.94 and 29.76 g each, respectively. Sub-fraction 3-4 evidenced a high level of unsaturation, indicative of the presence of methylidene malonate species, most likely a mixture of the 2.1.2; 2.2, and 2.1.1.2 species as well as dimers, trimers, oligomers and, possibly, some polymers. Other byproducts, such as glutarates and/or acetates were also likely present.

Example 15

21.17 g paraformaldehyde, 18.83 g copper (II) acetate hydrate, 39.54 g glacial acetic acid and 200 ml toluene were added to a 500 ml 3-necked flask equipped with a Dean-Stark trap with magnetic stirring at room temperature. The pot temperature was slowly raised to 90° C. Thereafter, 90 g diethyl malonate was added portion-wise via an addition funnel. The reaction temperature raised to 92° C. after ⅓ of the malonate was added and reflux was noted. The reaction was allowed to continue for 3 hours with water collecting in the Dean-Stark trap filled with toluene. The crude reaction product was allowed to cool and then filtered to remove the salts and then washed with 10×100 ml water portions. 0.47 g of hydroquinone and 0.47 g maleic acid were then added to the crude product. The crude product was then subjected to a solvent strip at 40-50° C. at 12-30 mmHg with a bath temp of 80° C. resulting in a yield of 73.3 g (82%).

The crude product was then subject to flash distillation wherein the crude product was added to a dry still pot in a 170° C. oil bath, the still pot containing 0.05 g of maleic acid and 0.5 g hydroquinone, via a pressure equalizing funnel at a rate of approximately 2 drops per second. The product was collected as light yellowish liquid at 90-95° C. at 0.8 mmHg. A total of 57.7 g of product (60% yield) was recovered and stabilized with 0.86 g 0.1 wt % sulfuric acid and 0.06 g (1000 ppm) hydroquinone.

The stabilized product was then subjected to fractional distillation with each collection having been treated with the sulfuric acid/hydroquinone stock solution, which yielded the following:
Fraction 1—45-49° C. @ 1.3 mmHg—yield 4.62 g
Fraction 2—50-55° C. @ 1.3 mmHg—yield 11.83 g
Fraction 3—56-63° C. @ 1.05 mmHg—yield 21.8 g
Fraction 4—68-75° C. @ 0.8 mmHg—yield 7.9 g, with 11.84 of a straw-colored residue.

Mass Spec and GC analysis showed fractions 1 and 2 to be the purest with fraction 3 having some saturation and fraction 4 showing very little unsaturation.

Example 16

A composite of crude 2.1.2 monomer made generally along the lines of the direct process set forth above except that malonate was the 2.1.2 malonate (the ethylcarbonyl-ethylcarbonylmethylcarbonyl malonate) instead of the diethyl ester was subjected to further purification. The crude product was added to a distillation flask that had been pretreated with approximately 4.68 ppm sulfuric acid and 1000 ppm hydroquinone, based on the amount of the crude 2.1.2 (935.15 g). The composite material was then subjected to fractional distillation yielding six fractions, the latter the still bottoms. All but the latter were then stabilized with 15 ppm trifluoroacetic acid and 1000 ppm hydroquinone based on the amount collected. Fractions 1 through 5 weighed 172.84, 155.16, 206.54, 215.07 and 157.63 g., respectively, for a 97% yield.

Example 17

A composite of crude 2.2 monomer made generally along the lines of the direct process set forth above was subjected to further purification. The crude product was added to a distillation flask that had been pretreated with approximately 12.1 ppm sulfuric acid and 1000 ppm hydroquinone, based on the amount of the crude 2.2 (621.1 g). The composite material was then subjected to fractional distillation yielding seven fractions, the latter the still bottoms. All were then stabilized with 15 ppm trifluoroacetic acid and 1000 ppm hydroquinone based on the amount collected. Fractions 1 through 6 weighed 92.82, 94.74, 78.15, 98.82, 108.89 and 101.28 g., respectively.

Example 18

21.17 g. paraformaldehyde, 18.83 g copper (II) acetate hydrate, 39.54 g. glacial acetic acid and 220 ml toluene were added to a 500 ml 3-necked flask equipped with a Dean-Starke trap with magnetic stirring at room temperature. Heat was applied slowly to achieve a 105° C. bath temperature (90° C. pot temperature). 90 g. of diethyl malonate was then added portion-wise via an addition funnel. An exotherm was noted with the temperature rising to 92° C. after ⅓ of the malonate was added. A reflux was noted and water was removed via a Dean-Stark trap filled with toluene at gentle reflux. A total of 14 ml of water was removed after 3 hours. The reaction mix was allowed to cool and thereafter filtered to remove salts and then washed with 10×100 ml water portions. 0.47 g maleic acid and 0.47 g hydroquinone are then added to the filtrate.

The filtrate is then subjected to a solvent strip at 40-50° C. @ 120-30 mm Hg—with a bath temp of 80° C. A crude liquid reaction product yield of 79.3 g (82%) was recovered. The crude reaction liquid product was then subjected to flash distillation by adding the crude product via a pressure-equalizing funnel at an approximate rate of 2 drops/sec to a dry still pot containing 0.05 g maleic acid and 0.05 g hydroquinone in a 170° C. oil bath. The collected crude product was received as a light yellowish liquid at 90-95° C. @ 0.8 mm Hg. Crude yield: 57.7 g (60%) (A). A second, conventional distillation was performed, as described in the preceding example, using cow fractions. The collection vessels were pretreated with 0.86 g 0.1 wt % sulfuric acid in ethanol (15 ppm) and 0.06 g hydroquinone (1000 ppm). Distillation was conducted at a bath temp of 130° C. The following fractions were collected:

Fraction I: 45-49° C. @ 1.3 mm, yield: 4.62 g.
Fraction II: 50-55° C. @ 1.3 mm, yield: 11.83 g.
Fraction III: 56-63° C. @ 1.05 mm, yield: 21.27 g.
Fraction IV: 68-75° C. @ 0.8 mm, yield: 7.90 g.
Remaining was 11.84 g of a straw-colored residue (R). Mass Spec and/or GC data on these fractions showed fractions I and II to be the purest, with fraction III showing some saturation, while fraction IV and the residue R showing very little unsaturation.

Example 19

143 g of the 2.1.2. malonate (82% pure), 25 g. paraformaldehyde, 2.99 g copper (II) acetate hydrate, 44 g. glacial acetic acid and 175 ml toluene were added to a 500 ml 3-necked flask equipped with a Dean-Starke trap with magnetic stirring at room temperature. Heat was applied slowly and an exotherm noted. Water was removed via the Dean-Stark trap filled with toluene at gentle reflux. A total of 20 ml of water was removed after 3 hours and a bath temperature of 155° C. An additional 175 ml of toluene was added and then the reaction product was washed with 10×150 ml 0.05N sulfuric acid portions. Sufficient amounts of 0.1 wt % sulfuric acid in ethanol and hydroquinone were then added bring the level of each to 15 ppm and 1000 ppm, respectively.

The crude reaction product was then subjected to a solvent strip by rotary evaporation at 100 mmHg while gradually raising the vacuum to 6 mmHg in an 80° C. bath. A crude liquid reaction product yield of 145.78 g was recovered. The crude reaction liquid product was then subjected to flash distillation by adding the crude product via a pressure-equalizing funnel at an approximate rate of 2 drops/sec to a dry still pot containing 2.15 g 0.1% sulfuric acid solution and 0.22 g hydroquinone in a 210° C. oil bath. 1.61 g of a fore cut boiling at 90-100° C. at 1.5 mmHg was removed. Thereafter, 48.31 g of a colorless liquid was recovered at 100-120° C. at 0.9 mmHg.

A number of additional general observations were also made in the course of the various runs performed for the direct process. For example, as noted in Example 15 above, a chromatogram of fraction 3 showed very little remaining acetic acid indicating that water washing may improve purity, or at least aid in the removal of residual acetic acid. Similarly, it did not appear necessary to wash the crude product with the methylene chloride prior to the distillation step where p-xylene is employed as the solvent. In the solvent evaporation step, it is preferred that atmospheric pressure solvent strips should be avoided in an effort to keep the distillation reaction temperatures below the boiling point of the desired product. Pot distillation seemed to provide higher purity products than thin film evaporation. Finally, an excess of formaldehyde or formaldehyde source may help reduce the formation of glutarates, a reaction byproduct.

While the present invention has been described with respect to aforementioned specific embodiments and examples, it should be appreciated that other embodiments utilizing the concept of the present invention are possible without departing from the scope of the invention. The present invention is defined by the claimed elements and any and all modifications, variations, or equivalents that fall within the spirit and scope of the underlying principles embraced or embodied thereby.

We claim:

1. A method of making a methylene malonate monomer said method comprising the steps of:
   a) reacting a malonic acid ester or malonic acid ester precursor with a source of formaldehyde, in the presence of a catalyst, alone or in further combination with an acid, a solvent or both an acid and a solvent, wherein a reaction phase polymerization inhibitor is added to the reaction mix prior to, concurrent with, or following the initial reaction of the malonic acid ester or its precursor, as applicable, with the formaldehyde source, said reaction phase stabilizer comprising at least one liquid phase primary anionic polymerization inhibitor, alone or in combination with at least one free radical polymerization inhibitor, and
   b) subjecting the reaction product of (a) to flash distillation to create a vapor phase containing the methylene malonate monomer and recovering the methylene malonate from the vapor phase wherein (i) the flash distillation is carried out in the presence of a separation phase polymerization inhibitor or (ii) the recovery vessel for the methylidene malonate end product contains a separation phase polymerization inhibitor or both (i) and (ii), said separation phase polymerization inhibitor comprising at least one liquid phase anionic polymerization inhibitor, alone or in combination with a free radical polymerization inhibitor.

2. The process of claim 1 wherein the flash distillation is conducted in a still pot or vessel and at least a portion of separation phase polymerization inhibitor is added pot or vessel prior to initiating flash distillation.

3. The process of claim 2 wherein at least a portion of the same or a different separation phase polymerization inhibitor is also added to the collection vessel for the methylidene malonate prior to initiating flash distillation.

4. The process of claim 3 wherein additional separation phase stabilizer is added to the methylidene malonate recovered from the flash distillation process.

5. The process of claim 2 wherein the anionic polymerization inhibitor of the separation phase polymerization inhibitor comprises at least one primary anionic polymerization inhibitor, at least one secondary anionic polymerization inhibitor or a combination thereof.

6. The process of claim 1 wherein the methylene malonate is recovered from the vapor phase in a collection vessel and at least a portion of a separation phase polymerization inhibitor is added to the collection vessel prior to initiating flash distillation.

7. The process of claim 6 wherein additional separation phase stabilizer is added to the methylidene malonate recovered from the flash distillation process.

8. The process of claim 6 wherein the anionic polymerization inhibitor of the separation phase polymerization inhibitor comprises at least one primary anionic polymerization inhibitor, at least one secondary anionic polymerization inhibitor or a combination thereof.

9. The process of claim 1 wherein each primary anionic polymerization inhibitor is a strong acid.

10. The process of claim 1 wherein each primary anionic polymerization inhibitor is independently selected from trifluoroacetic acid, sulfuric acid, maleic acid, perchloric acid and chlorosulfonic acid.

11. The process of claim 1 wherein the catalyst is a metal salt of a lower monocarboxylic acid.

12. The process of claim 1 wherein the catalyst is selected from copper(II) acetate, cupric acetate monohydrate, potassium acetate, zinc acetate, zinc chloracetate, magnesium chloracetate, magnesium acetate, and combinations of any two or more thereof.

13. The process of claim 1 wherein a combination of a catalyst and an acid is present and the acid is acetic acid, acetic acid anhydride, or glacial acetic acid.

14. The process of claim 1 wherein a solvent is present.

15. The process of claim 1 wherein the temperature of the reactants is elevated until an exotherm occurs.

16. The process of claim 15 wherein the reaction (a) is conducted at a temperature of about 105° C.

17. The process of claim 1 wherein the flash distillation is conducted at a temperature of from 170° C. to 210° C.

18. The process of claim 1 wherein the collected methylene malonate is subjected to a subsequent purification process.

19. The process of claim 18 wherein the subsequent purification process is selected from fractional distillation, solvent stripping, crystallization, precipitation, extraction, gel filtration, electrophoresis, foam fractionation, electromagnetic separation, thin film evaporation, press extraction, and chromatography as well as combinations of the foregoing.

20. The process of claim 1 wherein a combination of a catalyst and an acid is present.

21. The process of claim 1 wherein the malonate ester is employed.

22. The process of claim 21 wherein the malonate ester is of the general structure:

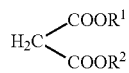

wherein $R^1$ and $R^2$ may be the same or different and represent H or a $C_1$ to $C_{18}$ hydrocarbon group or heterohydrocarbon group having one or more nitrogen, halogen, or oxygen atoms; provided that $R^1$ and $R^2$ are not both H.

23. The process of claim 22 wherein $R^1$ and $R^2$ are each independently a $C_1$ to $C_{10}$ linear or branched alkyl group; a $C_3$ to $C_6$ alicyclic group; a $C_2$ to $C_6$ alkenyl group; or a $C_2$ to $C_6$ alkynyl group; any of which may optionally be substituted with an ether, epoxide, halo, ester, cyano, aldehyde, ketone or aryl group.

24. The process of claim 22 one or both of $R^1$ and $R^2$, which may be the same or different, are of the formula:

$$—(CH_2)_n—COOR^8 \quad (IV)$$

wherein $R^8$ is a $C_1$ to $C_6$, lower alkyl and n is an integer of from 1 to 5.

25. The process of claim 1 wherein the separation phase polymerization inhibitor is added to the crude product prior to conducting the flash distillation.

26. The process of claim 1 wherein the reaction phase stabilizer and the separation phase polymerization inhibitor are the same.

27. The process of claim 1 wherein the reaction phase stabilizer and the separation phase polymerization inhibitor are different.

* * * * *